United States Patent [19]
Dow et al.

[11] Patent Number: 5,834,446
[45] Date of Patent: Nov. 10, 1998

[54] NERVE PROCESS GROWTH MODULATORS

[75] Inventors: Kimberly E. Dow; Boris I. Gorine; Richard J. Riopelle; Gregory Thatcher, all of Kingston, Canada

[73] Assignee: Queen's University at Kingston, Kingston, Canada

[21] Appl. No.: 668,189

[22] Filed: Jun. 21, 1996

[51] Int. Cl.$^6$ ........................................ A01N 43/04
[52] U.S. Cl. ................ 514/58; 536/45; 536/46; 536/47; 536/48; 536/102; 536/103
[58] Field of Search ....................... 536/102, 103, 536/45, 46, 47, 48; 514/58

[56] References Cited

U.S. PATENT DOCUMENTS 5,019,562  5/1991  Folkmanet et al. .
5,464,827  11/1995  Soll .

FOREIGN PATENT DOCUMENTS 0627446  12/1994  European Pat. Off. .
WO 95/07087  3/1995  WIPO .

OTHER PUBLICATIONS

Szetli, J., "Cyclodextrins and their inclusion complexes", Ackademiai Kiado, Budapest, 1982.
Hanessian, S., Benalil, A., Laferriere, C., *J. Org. Chem.*, 1995, 60, 4786.
Ashton, P.R., Koniger, R., Stoddart, J.F., Alker, D., Harding, V.D., *J. Org. Chem.*, 1996, 61, 903.
Boger, J., Corcoran, R.J., Lehn, J–M., *Helv. Chim. Acta*, 1978, 61, 2190.
Khan, A.R., D'Souza, V.T., *J. Org. Chem.*, 1994, 59, 7492.
Boger, J., Brenner, D.G., Knowles, J.R., *J. Am. Chem. Soc.*, 1979, 101, 7630.
Baer, H.H., Shen, Y., Gonzalez, F.S., Berenguel, A.V., Garcia, J.I., *Carbohydr. Res.*, 1992, 235, 129.
Fugedi, P., *Carbohydr. Res.*, 1989, 59, 7511.
Takeo, K., Mitoh, H., Uemura, K., *Carbohydr. Res.*, 1989, 187, 203.
Yoon, J., Hong, S., Martin, K.A., Czarnik, A.W., *J. Org. Chem.* 1995, 60, 2792.
Moriya, T., Kanda.,A., Matumoto, K.,m Otake, T., Mori, H., Morimoto, M., Ueba, N., Kunita, N., *J. Med. Chem.*, 1991, 34, 2301.
Alker, D., Ashton, P.R., Harding, V.A., Koniger, R., Stoddart, J.F., White, A.J.P., Williams, D.J., *Tetrahdr. Lett.*, 1994, 35, 9091.
Baer, H.H., Berenguel, A.V., Shu, Y.Y., Defaye, J., Gadelle, A., Gonzalez, F.G., *Carbohydr. Res.*, 1992, 228, 307.
Moriya et al., *J. Med Chem.*, vol. 34, No. 7, pp. 2301–2304 (1991).
Gadelle, A. et al., "Selective Halogenation at primary positions of cyclomaltooligosaccharides and a synthesis of per–3, 6–anhydro cyclomaltooligosaccharides", Abstract No. XP000606849 in *Angewandte Chemie, Intl. Ed.* 30(1):78–80 (1991).
Lu, D.–P. et al., "Synthesis of 6–deoxymaltooligosaccharides and a study of their lipid–binding properties", *Carbo. Res.* 160: 171–184 (1987).
Åkerfeldt, K.S. et al., "Synthesis and per–functionalization of heptakis(6–O–carboxymethyl–2,3–di–O–methyl)cyclomaltoheptaose", *Tetrahedron Letts.* 35(26):4489–4492 (1994).
Szurmai, Z. et al., "Halogen azide displacement to prepare some symmetrically substituted β–cylodextrin derivatives", Abstract No. XP000160863 in *Starch Starke* 42(11):447–449 (1990).

*Primary Examiner*—James O. Wilson
*Attorney, Agent, or Firm*—Richard J. Hicks; Carol Miernicki Steeg

[57] ABSTRACT

Nerve process growth modulation can be achieved using derivatized cyclodextrins. Processes for making sulfated and aminated β-cyclodextrin derivatives are also described in which a compound of the formula $R''_2$ NCH $X^{'+}X^{'-}$ where $R^-$ is an alkyl containing 1–5 carbon atoms and X is selected from bromine and iodine is used to halogenate the cydodextrin.

14 Claims, 3 Drawing Sheets

NERVE PROCESS GROWTH MODULATORS

FIELD OF INVENTION

This invention relates to nerve process growth modulation using novel cyclomalto-oligosaccharides, commonly known as cyclodextrins, and to methods making the novel oligosaccharides. More particularly this invention relates to the use of novel sulfated and aminated β-cyclodextrin derivatives as potent modulators of nerve process growth.

BACKGROUND OF INVENTION AND PRIOR ART

Cydodextrins (CD or CDS) are cyclic oligosaccharides consisting of at least six and up to about twelve α(1,4) linked D-glycopyranose units. These compounds have the formula

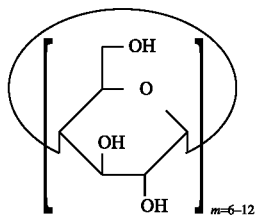

The cyclic nature of CDS leads to a toroidal shape with a primary face (consisting of primary hydroxyl moieties at $C_6$), a secondary face (consisting of secondary hydroxyl moieties at $C_2$ and $C_3$) and a cavity which is normally considered to be hydrophobic in nature. The external surface of the molecule is more hydrophilic.

The nature of the cavity results in the ability of CDS to form non-covalent inclusion complexes in which, most commonly, an added but separate biologically active molecule is contained within the toroidal cavity. Numerous such complexes have been described which find utility as pharmaceuticals, veterinary compounds, cosmetics, food and flavour additives and the like. These complexes have in common the feature that the cyclodextrin is a "carrier" for a separate active molecular entity modification and derivatization of cyclodextrins has also been reported in order to alter the properties of cyclodextrin as a carrier (or otherwise encapsulating) molecule. Typical of such derivatives are the CD sulfates and other water soluble derivatives described in U.S. Pat. No. 5,019,562, issued 28 May 1991 to Folkman et al. The present invention is not, however, concerned with CDS as "carriers" in which complexes are formed, but rather with the concept that the CD is a molecular scaffold in which a number of pendant groups may be attached to the primary and secondary faces. For example, in γ-cyclodextrin, there are eight points of attachment on the primary face and sixteen on the secondary face. In a homogeneous derivative, all primary face sites would have an identical pendant chemical group covalently attached, and all secondary face sites would have identical, but different from those on the primary face, pendant chemical groups attached.

The primary face pendant groups are designed to confer biological activity on the derivatized CD molecule itself The secondary face pendant groups are designed specifically to alter the properties, such as solubility, membrane permeability and bioavailability, of the derivatized cyclodextrin. The pendant groups on the primary face may be chosen to result in a derivatized CD which is either ionic or cationic at any pH in aqueous solution. For example, nitrogen-containing groups may bear a positive charge whereas sulfur-containing groups may carry a negative charge.

Some derivatives of CD, bearing pendant groups at the primary face, prepared as homogeneous CD derivatives have been previously described. Similarly, amine nitrite and sulfonate derivatives of CDs have also been described. However, the methods of making these compounds generally require arduous purification steps and are generally unsatisfactory.

OBJECT OF INVENTION

It is one object of the present invention to provide an improved process for preparing homogeneous derivatives of cyclodextrins.

Another object of this invention is to provide small molecule proteoglycan modulators of nerve process growth.

BRIEF STATEMENT OF INVENTION

Thus, by one aspect of this invention there is provided a process for producing homogeneous cyclodextrin derivatives of the formula

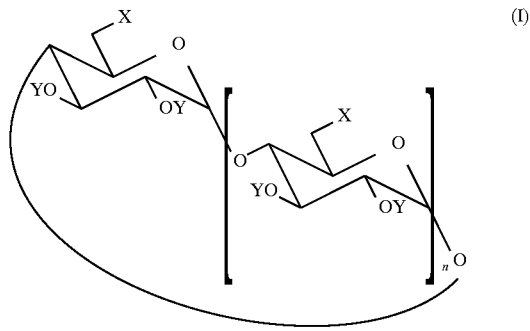

in which n is an integer from 5 to 12;

X is selected from the group consisting of $NH_2$, $NH_3Q$, $NH_3R$, $CH_2NH_2$, $CH_2NH_3Q$, $CH_2\ NH_3R$, $SR^1$ and $SO_3^-Z^+$;

Y is selected from H, alkyl or carboxyl ester chains containing from 1–20 carbon atoms which may contain nitrogen and unsaturations;

where R is an alkylamino or alkylammonium substituent containing 1–20 carbon atoms, 1–10 nitrogen atoms and 4–80 hydrogen atoms, and with 1–10 counterions, and including groups in which C,H and N are present in a heterocyclic ring;

$R^1$ is H or R;

Q is an anionic counterion; and

Z is a cation selected from the group consisting of sodium potassium or trialkylammonium;

comprising reacting a cyclodextrin as defined above but bearing free hydroxyl groups at the carbon-6 position with a compound of the formula:

where R" is an alkyl containing 1–5 carbon atoms; and X' is a halogen selected from the group consisting of bromine and iodine, so as to produce a halogenated derivative, and converting said halogenated derivative to a selected said homogeneous cyclodextrin derivative by substitution or exchange of said X' at carbon 6.

By another aspect of this invention there is provided a homogeneous cydodextrin derivative of the formula

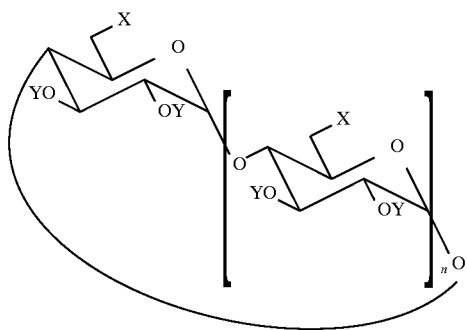

in which n is an integer from 3 to 12;

X is selected from the group consisting of $NH_2$, $NH_3Q$, $NH_3R$, $CH_2NH_2$, $CH_2NH_3Q$, $CH_2 NH_3R$, $SR^1$ and $SO_3^-Z^+$;

Y is selected from H, alkyl or carboxyl ester chains containing from 1–20 carbon atoms which may contain nitrogen and unsaturations;

where R is an alkylamino or alkylammonium substituent containing 1–20 carbon atoms, 1–10 nitrogen atoms and 4–80 hydrogen atoms, and with 1–10 counterions, and including groups in which C,H and N are present in a heterocyclic ring;

$R^1$ is H or R;

Q is an anionic counterion; and

Z is a cation selected from the group consisting of sodium potassium or trialkylammonium;

By another aspect of this invention there is provided a method for modulating nerve process growth comprising administering to a patient in need thereof a homogeneous cyclodextrin derivative of the formula

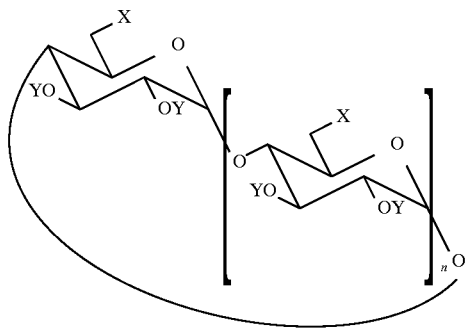

in which n is an integer from 5 to 12;

X is selected from the group consisting of $NH_2$, $NH_3Q$, $NH_3R$, $CH_2NH_2$, $CH_2NH_3NH_3Q$, $CH_2NH_3R$, $SR^1$ and $SO_3^-Z^+$;

Y is selected from H, alkyl or carboxyl ester chains containing from 1–20 carbon atoms which contain nitrogen and unsaturations;

where R is an alkylamino or alkylammonium substituent containing 1–20 carbon atoms, 1–10 nitrogen atoms and 4–80 hydrogen atoms, and with 1–10 counterions, and including groups in which C, H and N are present in a heterocyclic ring;

$R^1$ is H or R;

Q is an anionic counterion; and

Z is a cation selected from the group consisting of sodium potassium or trialkylammonium in admixture with a pharmaceutically acceptable carrier therefore.

DETAILED DESCRIPTION OF PREFERRED EMBODIMENT

Figure 1:
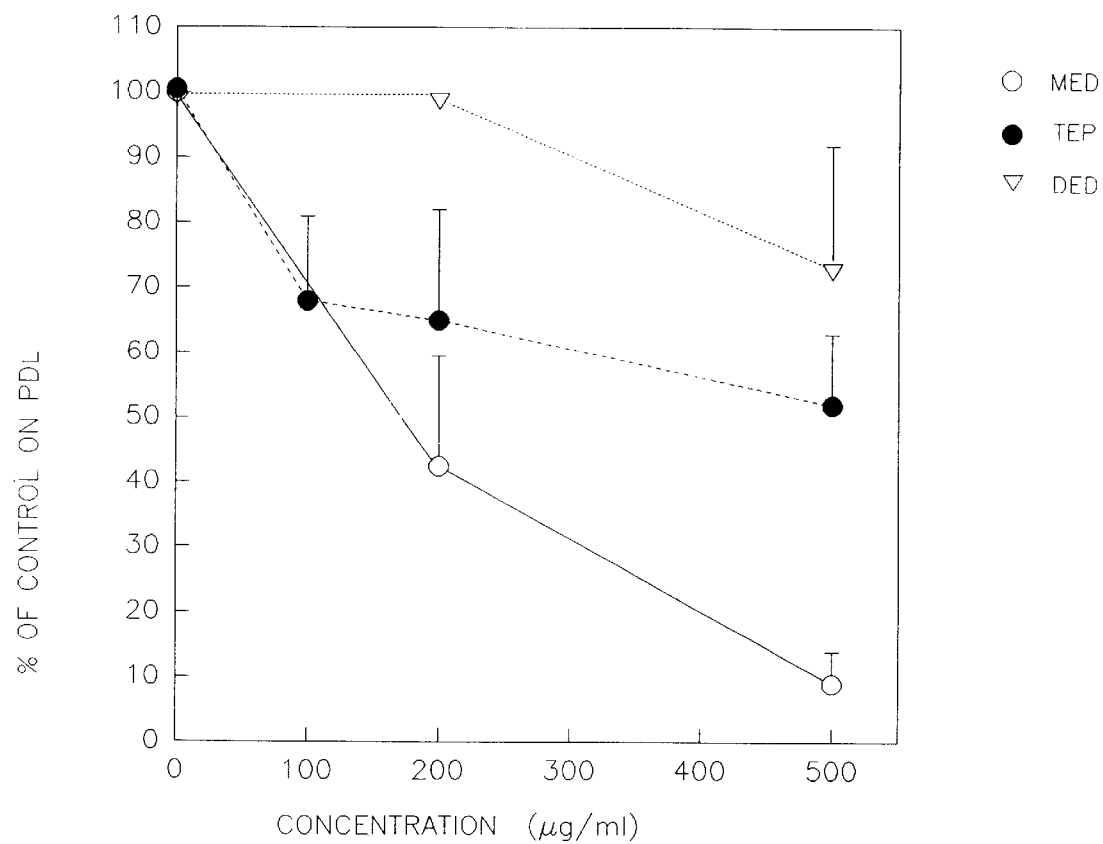
FIG. 1 is a graph illustrating inhibition of neurite growth by SPAβCD in solution. Enriched sensory neurons from ED8 chick DRG were cultured on PDL in the presence of 1 ng/ml NGF and the SPAβCDs in solution at the indicated final concentrations. Neurite growth was scored blind at 18–24 hours after seeding the cells. Results are expressed as a percent of control (no additives) and are the mean of two experiments (quadruplicate determinations). Error bars represent standard deviation from the mean.

The CD derivatives contemplated for preparation by the present invention have the following general formula:

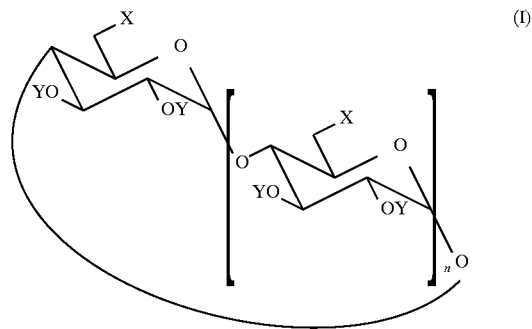

in which n is an integer from 5 to 12;

X is selected from the group consisting of $NH_2$, $NH_3Q$, $NH_3R$, $CH_2NH_2$, $CH_2NH_3Q$, $CH_2NH_3R$, $SR^1$ and $SO_3^-Z^+$;

Y is selected from H, alkyl or carboxyl ester chains containing from 1–20 carbon atoms which may contain nitrogen and unsaturations;

where R is an alkylamino or alkylammonium substituent containing 1–20 carbon atoms, 1–10 nitrogen atoms and 4–80 hydrogen atoms, and with 1–10 counterions, and including groups in which C, H and N are present in a heterocyclic ring;

R¹ is H or R;

Q is an anionic counterion;

and Z is a cation selected from the group consisting of sodium potassium or trialkyl-ammonium;

As will be appreciated, these CD derivatives are homogeneous, all primary face sites have covalently attached, identical, pendant groups and all secondary face sites have pendant groups identical to each other but different from those on the primary face sites.

The above compounds can be produced, according to the present invention, by halogenation of CD or a derivative of CD modified at the secondary face in which all carbon-6 positions of the primary face are halogenated. The essential feature of this process is the use of a reagent of the formula

$$R''_2 NCH X'^+ X'^- \quad (2)$$

where R" is an alkyl containing

1–5 carbon atoms; and

X' is selected from bromine and iodine.

Use of this reagent reduces the number of processing steps, raises the yield of product and produces a homogeneous product.

The starting material for halogenation may be a CD or CD derivative modified at the secondary face. Thus, any CD bearing pendant groups Y (as described above) but underivatized at the primary face, that is bearing free hydroxyl groups at the carbon-6 position, may be converted to halogenated CD derivatives using reagent 2. These conversion products are described by the same formula as (1) with the exception that X is either iodine or bromine. These halogenated CD derivatives can then be converted to the desired cationic or anionic CD derivative by substitution or exchange of the halogen at carbon-6 with a different, selected, chemical group. For example, anionic sulfonate CD derivatives requires exchange of halogen with a sulfonyl group ($SO_3^-$) and may be effected by reacting the halogenated CD with an all[]i metal sulfite salt, under pressure, to yield a homogeneous CD derivative in which all the primary face carbon -6 positions bear a sulfonyl group. Cationic CD derivatives can be prepared by any one of four methods. Firstly, the halogenated CD may be reacted with an alkali metal azide salt and reduced with triphenylphosphine followed by basic work up to yield a homogeneous CD derivative in which all primary face carbon-6 positions bear an amino($NH_2$) group. Acidification of the amino CD derivative allows isolation of a cationic amino CD derivative as a salt. The amino CD derivative may also be reacted with an aldehyde or acetal to yield an imino CD derivative, a Schiff base, in which all primary face carbon-6 positions bear a nitrogen doubly bonded to carbon, in an imine functionality. The aldehyde or acetal is selected so as to yield a product conforming to formula (1).

Further reductions of the imine functionality of the Schiff base produces a homogeneous amine CD derivative in which all primary face carbon-6 positions bear a nitrogen which is part of an amine functionality. The imino or amino CD derivatives may be acidified to produce a salt, which may contain counterions to the cationic CD derivative as described in formula (1).

Secondly, the halogen of a halogenated CD derivative may be exchanged with a nitrile or cyano group (—CN) by reaction with an ally metal cyanide salt to yield a homogeneous cyano-CD derivative in which all the primary face carbon-6 positions bear a nitrile group. Reduction of the nitrile group yields a homogeneous amino CD derivative in which all the primary face carbon-6 positions bear an aminomethylene group (—$CH_2NH_2$). Acidification of the aminomethylene CD derivative isolates a cationic amino CD derivative as a salt. Alternatively, further reaction of the aminomethylene CD derivative, as described above for the amino CD derivative, yields cationic CD derivatives conforming to formula (1).

Thirdly, a halogenated CD derivative may be reacted with thiourea to produce a thiouronium CD derivative in which all primary face carbon-6 positions bear a thiouronium ($SC(NH_3)_2$ X; where X is I or Br) group. Acidification results in isolation of a thiouronium salt of the CD derivative. Hydrolysis or alcoholysis of the thiouronium salt gives a homogeneous mercapto CD derivative in which all the primary face carbon-6 positions bear a mercapto or thiol group (—SH). Cationic derivatives of formula (1) can be prepared from the mercapto CD derivative by reaction with an alkyl halide (where the halide is Cl, Br or I). The product of this reaction can be isolated as a homogeneous mercaptoamine CD derivative, conforming to formula (1) in which all primary face carbon-6 positions bear a sulfur which is part of a sulfide functionality. The alkyl group of the alkyl halide may contain nitrogen, unsaturated and aryl groups, but is limited to conform to a final product described by formula (1).

Acidification produces a mercaptoamine CD derivative salt, which may contain counterions to the cationic CD derivative, as described in formula (1).

Fourthly, a halogenated CD derivative may be reacted with an excess of the appropriate amine, $H_2NR$, to yield a product corresponding to formula (1).

Example 1

Per-2,3-dimethyl-per-6-amino-6-deoxy-CD HCl salt (Formula 1: X=$NH_3Cl$; Y=$CH_3$; n=5–7). The bromination reagent, [$ME_2NCHBr$]⁺Br⁻ was prepared by addition of $Br_2$ dropwise to triphenylphosphine in DMF. The reaction mixture was cooled to 0° C. and allowed to stand forming a precipitate, which was filtered to isolate the imminium reagent as a white crystalline solid. After washing with cold DMF, the solid was dissolved in DMF and the CD (freshly dried) added to the solution. The mixture was heated for 18 hr at 80° C. with a drying tube, allowed to cool and an aliquot of sodium methoxide solution (3M) added. Solvent was removed at reduced pressure to yield the product as a syrup. Water was added and after stirring the precipitate was filtered and washed with water to yield the per-6-bromoCD product in 95–98% yield.

Per-6-azidoCD ws obtained from reaction of the per-6-bromoCD with sodium azide (1.3n eq.; weher n=6–8) in DMF at 65° C. for 24 hr. Solvent was evaporated and the residue added to water. The precipitate was filtered and washed with acetone to give product in 94–98% yield.

The per-2,3-dimethyl-per-6-amino-6-deoxyCD derivative of βCD (MeβCDA) was prepared by addition of methyl iodide (40 eq.) to a solution of per-6-azido-6-deoxyβCD and NaH (30 eq.) in DMF. The reaction mixture was stirred for 24 hr at R.T., methanol added and the mixture concentrated under vacuum. Ice-water was added and the resulting precipitate collected and dried. MeβCDA was obtained as the per-6-ammonium chloride salt by reduction of the azide with triphenylphosphine in dioxane followed by work-up with ammonium hydroxide solution and isolation as previously described. The product was obtained as a white solid in 92% isolated yield, calculated from the azide. These synthetic strategies yield CD derivatives, homogeneous by ¹H and ¹³C NMR spectroscopy (FIG. 1) without recourse to chromatography.

Example 2

Per-6-[N,N-dimethyl-2-aminoethylamino]-6-deoxy-CD HCl salt (or HCl salt of $(CH_3)_2NCH_2CH_2NH_2$ derivative; Formula 1: $X=NHCH_2CH_2NMe_2.2HCl$; $Y=H$; $n=5-7$) was synthesized from the corresponding per-6-bromo-6-deoxyCD, prepared as described above. The per-6-bromo-6-deoxyCD (1 mmol) in N,N-dimethylethylenediamine (10 ml) was refluxed for 24 hr then evaporated to dryness under vacuum. The residue was dissolved in water and acidified to pH 4 using HCl (dil.). Solvent was removed under vacuum and the resulting solid washed with successive portions of boiling ethanol to yield the product as a highly hygroscopic crystalline powder in 85–96% yield.

drying in an isolated yield of 87–92%. Alternatively, the per-6-amino-6-deoxyCD, may be obtained from the initial isolated precipitate by washing with successive portions of benzene and drying under high vacuum.

To a suspension of per-6amino-6-deoxyCD (0.448 mmol) in dry DMF (5 ml) was added pyridine-2-carboxaldehyde (7.5 eq.). The suspension was stirred for 3 hr at room temperature, over which time an homogeneous orange solution resulted. Addition of acetone gave a precipitate which was filtered, washed and dried under vacuum to give the per-6-imino-6-deoxyCD derivative in 75–82% isolated yield. Reduction of the CD-imine was facile on stirring with sodium borohydride (10 eq.) in methanol (8 ml) at −78° C. for 3 hr.

TABLE

Spectroscopic data for CD derivatives; Using Formula 1: 1 (X = Br; Y = H) 2 (X = $N_3$; Y = H) 3 (X = $NH_3Cl$; 4 (X = CN; Y = H) 5 (X = $SCN_2H_4Br$; Y = H) 6 (X = SH; Y = H) 7 (X = $NH_3Cl$; Y = Me) 8 (X = $NHCH_2CH_2NMe_2.2HCl$; Y = H) 9 (X = $NHCH_2C_5H_4N.HCl$; Y = H).
$^{13}C$ NMR shifts (ppm)

| | FAB-MS[a] | C1 | C2 | C3 | C4 | C5 | C6 | C(N) | solvent |
|---|---|---|---|---|---|---|---|---|---|
| 1α | 1351 | 101.84 | 71.62 | 72.49 | 84.70 | 70.66 | 34.76 | — | DMSO |
| 2α | 1096[c] 1047 | 101.81 | 71.61 | 72.76 | 83.44 | 70.45 | 51.40 | — | DMSO |
| 3α | 967[b] | 101.37 | 71.37 | 72.66 | 82.56 | 68.04 | 40.44 | — | $D_2O$ |
| 5α | — | 100.97 | 70.82 | 72.04 | 84.41 | 70.62 | 33.11 | 171.11 | $D_2O$ |
| 6α | 1070 | 101.84 | 71.50 | 72.78 | 85.04 | 71.86 | 26.10 | — | DMSO |
| 1β | 1576 | 102.09 | 72.04 | 72.28 | 84.62 | 71.01 | 34.43 | — | DMSO |
| 2β | 1333[c] 1284 | 102.03 | 71.99 | 72.58 | 84.62 | 71.01 | 34.43 | — | DMSO |
| 3β | 1128[b] | 101.65 | 71.86 | 72.40 | 82.44 | 68.01 | 40.47 | — | $D_2O$ |
| 4β | 1198 | 102.13 | 71.86 | 72.18 | 85.34 | 67.03 | 20.66 | 118.13 | DMSO |
| 5β | — | 101.53 | 71.30 | 71.88 | 84.24 | 70.83 | 32.83 | 170.96 | $D_2O$ |
| 6β | 1247 | 102.19 | 72.29 | 72.54 | 84.95 | 72.01 | 25.98 | — | DMSO |
| 1γ | 1825[c] | 102.02 | 72.18 | 72.26 | 84.05 | 71.02 | 34.38 | — | DMSO |
| 2γ | 1521[c] 1472 | 102.03 | 72.23 | 72.44 | 82.65 | 70.44 | 51.44 | — | DMSO |
| 3γ | 1290[b] | 100.67 | 71.86 | 72.07 | 81.03 | 67.78 | 40.46 | — | $D_2O$ |
| 5γ | — | 101.75 | 71.74 | 71.56 | 84.09 | 70.91 | 32.71 | 171.00 | $D_2O$ |
| 6γ | 1426 | 102.19 | 72.42 | 72.51 | 84.44 | 72.09 | 25.89 | — | DMSO |
| 7β | 1323 | 97.79 | 79.42 | 79.64 | 79.84 | 67.76 | 40.11 | | $D_2O$ |
| | other | carbons | 60.13 | 58.21 | | | | | |
| 8β | 1624 | 99.68 | 70.51 | 71.00 | 79.84 | 66.76 | 47.72 | | $D_2O$ |
| | other | carbons | 51.99 | 45.26 | 42.09 | | | | |
| 9β | 1536[c] | 102.55 | 72.99 | 73.6 | 83.05 | 69.16 | 50.66 | | $D_2O$ |
| | other | carbons | 148.12 | 146.54 | 145.17 | 129.72 | 129.22 | 50.01 | |

[a]Positive ion detection; Cs⁺ ion source. Molecular ion peaks corresponding to the most intense isotopic m/z ratio are reported. Isotoper distributions and ratios are compatible with structure assignment. Figures in italics refer to $(M - NH_2 + 2H)^+$:
[b]Free amines used for MS analysis.
[c]M + Na⁺ parent ion.

Example 3

Per-6-[methylene-2-pyridyl-amino]-6-deox-CD (Formula 1: $X=NHCH_2C_5H_4N$; $Y=H$; $n=5-7$) was prepared from the corresponding per-6-azido-6-deoxyCD. Per-6amino-6-deoxyCD was obtained by reduction of the azide with triphenylphosphine (3n eq.) in DMF with stirring at room temperature for 1.5 hr followed by dropwise addition of concentrated ammonium hydroxide solution to the reaction mixture and continued stirring for 15 hr. Solvent was evaporated and ethanol added to the residue. The resulting precipitate was filtered, washed with ethanol and added to a small volume of water. Careful acidification with dil. HCl to pH 4 gave a solution of the water-soluble CD-ammonium chloride salt from which contaminants can be removed by filtration. The CD-ammonium salt may be isolated by reduction of the resulting filtrate under vacuum and subsequent The desired product was isolated in quantitative yield, by precipitation with diethyl ether, filtration, washing with ether and drying under vacuum.

Compounds prepared in accordance with the above protocols have been evaluated for their role in adhesion and/or inhibition of neurite extension by nerve growth factor (NGF)-responsive cells.

It has been previously demonstrated that heparin sulfate proteoglycans (HSPG) of neuronal origin have neurite promoting activity either when complexed to the neuronal cell surface, or as immobilized substrates. It has also been demonstrated that the neurite growth promoting properties of neuronal HSPG's involve the complex carbohydrate side chains known as glycosaminoglycans, and that the degree of sulfation of these GAG's is critical to their neurite promoting activities.

In the spinal cord of embryo chick, during the window of permissiveness for regenerative growth, the milieu encountered by descending axons of brainstem neurons has a high HS/CS ratio, and neurite-promoting HSPG's in extracts of spinal cord are present in high titre. Alternatively, the milieu encountered by regenerating axons during the non-permissive period for axonal regrowth in the chick embryo spinal cord is enriched for chondroitin sulfate proteoglycans (CSPG's), and blockade of the effects of CSPG from extracts of spinal cord from the non-permissive period uncovers a permissive milieu for neurite growth. These observations add to a growing literature on the relative growth inhibitory effects of the CSPG's during development and regeneration of the nervous system.

Proteoglycans complexed to the neuronal cell surface or immobilized within the extra-neuronal environment interact via sulfate or carboxylate groups with glycosaminoglycan binding domains of the extracellular space that are found as specific domains within known adhesion proteins. While the primary amino acid sequences of such domains are heterogeneous, they share a consensus structure comprised of basic and hydrophobic/non-polar epitope repeats.

To mimic such structures so as to develop small molecule modulators of PG-mediated neuronal adhesion and neurite growth, the CD derivatives described above have been used in assays of neuronal adhesion and neurite growth, and compared with known complex carbohydrates to elucidate the glycosaminoglycan (GAG) specificity of their effects.

MATERIALS AND METHODS

Substrate preparation

The wells of the plastic tissue culture plates are treated by incubating them overnight at 37 C with 5 $\mu$l (Terasalci plates) or 30 $\mu$l (96 well) of sterile aqueous solution of the SPA-$\beta$CDs or PDL.

Before seeding the cells, the plates are washed twice with sterile distilled water and rinsed once with serum-free medium.

Cell culture

PC12 (rat pheochromocytoma) cells were obtained from ATCC and maintained in polystyrene culture dishes (Corning) in RPMI (Gibco) containing 10% heat inactivated donor horse serum and 5% fetal calf serum (Wisent). Cells were subcultured weekly at approximately 1:8. Cells were not used beyond 25 passages from ATCC stock and were revived from frozen stock when required. "Primed" PC12 cells were exposed to 50 ng/ml NGF (Cedarlane) in serum containing medium for 5 days before use.

Acid phosphatase assay for cell adhesion

Adhesion is evaluated by a colorimetric assay which measures the lysosomal acid phosphatase to determine cell number (Connolly et al., 1986) modified by Ueda et al. (1994) for use with cultured neuronal cells.

PC12 cells are seeded in serum-free medium in treated wells of a 96 well plate, (6000–9000 cells per well) and allowed to adhere at 4° C. for 60 minutes. The medium is then removed and the wells are washed gently with 100 $\mu$l of PBS. 100 $\mu$l of assay buffer (0.1M sodium acetate pH 5.5, 0.1% Triton X-100 and 10 mM p-nitrophenyl phosphate—Sigma 104 substrate) is added to each well. Plates are incubated at 37° C. for 2 hours. The reaction is stopped by the addition of 10 $\mu$l of 1M sodium hydroxide and the color development measured at 405 nm in a Titertek microplate reader.

Assay of neurite growth

Dissociated cells enriched for sensory neurons from DRG of ED8 chick were prepared as described in detail previously (Sutter et. al., 1979). Cells were seeded into the treated wells of Terasalci plates at a density of 900–1200 cells per well in supplemented Ham's F12 medium with 5% fetal calf serum and NGF at a final concentration of 1 ng/ml. The cells are incubated at 37° C., 5% $CO_2$ overnight. The wells are scored blind at 18–22 hours for neurite growth by counting all cells on the lower horizontal surface of the wells, which is approximately 15% of the surface area of the top of the tapered wells. Each experiment includes quadruplicate determinations for each treatment.

When the derivatized cyclodextrins were added to the neurons at the time of seeding in Terasald wells, they exhibited inhibitory activity towards NGF-mediated neurite growth.

The tetradecasulfated $\beta$-yclodextrin was the most potent inhibitor. Of the amine-derivatized $\beta$-yclodextrins, "H" appeared to be the least inhibitory. The parent, underivatized $\beta$-cyclodextrin, did not affect neurite extension by the cells, and at the concentration tested, the free amines "G", "H" and "I" (250 $\mu$M) did not substantially reduce the percentage of cells that were neurite bearing. However, the effect on overall viability by the free amines at this concentration requires further investigation.

Cyclodextrins as templates for neurite growth

I. With NGF alone

When incubated on the polystyrene wells overnight at 37° C., 4 of the 6 derivatized cydodextrins were found to interact with the plastic surface in a manner that permitted the DRG neurons to disperse and extend neurites in response to NGF, in a fashion similar to that seen with poly-D-lysine treatment of the Terasald wells.

The cyclodextrins were dissolved in water at a nominal concentration of 10 mg/ml and filter sterilized. 5 $\mu$l of the solution was aliquoted into wells of Terasald plates and the plates incubated in a $CO_2$ humidified incubator overnight. Prior to seeding the cells, the wells are washed twice with sterile water and rinsed with culture medium. When cultured on plastic (treated with water), the cells do not disperse evenly on the available surface. The phase bright cells cluster and the result is sparse clumps of rounded cells atop neurite bearing cells. Conversely, when poly-D-lysine is used as a substrate, the cells disperse uniformly at the bottom of the well with individual cells clearly defined.

Four of the amine-derivatized $\beta$-cyclodextrins could serve as a substrate for neurite growth, with cells morphology and extent of neurite growth similar to that seen with poly-D-lysine as a substrate. The growth response on wells treated with cyclodextrin "h" did not differ from that on the plastic surface, and the sulfated cyclodextrin did not permit neurite growth above blank levels (no NGF).

Wells treated with 5 mM aqueous solutions of the free amines "G", "H" and "I" did not exhibit a response different from plastic alone (data not shown).

ii. Effects of mixed sulfated glycosaminoglycans in solution

Preliminary experiments were carried out with poly-D-lysine or the amine-cyclodextrins as substrate. DAG neurons were seeded in the presence of ng/ml NGF and co-incubated with 10 $\mu$g/ml chondroitin sulfate or heparan sulfate, with the following results:

Adhesion

Adhesion was assessed by assaying for acid phosphatase released by cells remaining in treated wells. The values obtained were compared to control adhesion of cells on plastic treated with water.

TABLE 1

| | 8 day chick DAG | PC 12 naive | PC12 NGF-primed 7 days |
|---|---|---|---|
| pdl (0.1 mg/ml) | + | + | + |
| 14βSO₄CD (10 mg/ml) | – | – | – |
| parent βCD (5 mg/ml)* | | – | – |
| "E" βCD (10 mg/ml) | | + | + |
| "F" βCD (10 mg/ml) | | + | + |
| "G" βCD (1 mg/ml)** | + | + | + |
| "H" βCD (10 mg/ml) | – | – | – |
| "E" free (amine (5 mM) | | – | – |
| "F" free (amine (5 mM) | | – | – |
| "G" free (amine (5 mM) | | – | – |

– no different from value obtained on untreated plastic
+ greater than value obtained on plastic (p > .05 t-test)
*the parent β cyclodextrin was not soluble in water at 10 mg/ml
**1 mg/ml nominal concentration of cyclodextrin "G" was as effective as 10 mg/ml.

| | % OF ITS CONTROL (NO ADDITIVE) ADDITIVE: | |
|---|---|---|
| SUBSTRATE | CHONDROITIN SULFATE | HEPARAN SULFATE |
| "E" | 93 | 59 |
| "F" | 112 | 81 |
| "G" | 111 | 50 |
| "H" | 250 | 151 |
| "I" | 114 | 33 |
| pdl | 141 | 93 |

Amine pendant groups designated by capital letters:

"E"—CH₃NHCH₂CH₂NH₂
"F"—H₂NCH₂CH₂NHCH₂CH₂NH₂
"G"—HN(CH₂CH₂NHCH₂CH₂NH₂)₂
"H"—(CH₃CH₂)₂NCH₂CH₂NH₂
"I"—(CH₃)₂NCH₂CH₂NH₂

A Leitz Diavert inverted microscope equipped with phase optics was used to score neurite growth. A neurite was scored as such if its calibre from origin to terminal was approximately the same and the length was equal to or greater than 1.5 cell body diameters. Data expresses neurite bearing cells as a percent of total viable cells on the lower surface.

Statistical analysis

Data was analysed using Sigma Stat version 1.01 (Jandel Scientific) by one way anova (α=0.05) with Student-Neuman-Keuls or Dunnetts-t post test.

1. Soluble polyammonium—βcyclodextrins (SPA-BCD's) block NGF-mediated neurite growth on poly-D-lysine In the presence of NGF primary sensory neurons extend processes on a poly-D-lysine substrate. At 18–22 hours four SPA-BCD's inhibited neurite growth in a concentration dependent fashion (FIG. 1). At 500 μg/ml the rank ordering of inhibition of neurite growth was E>G>K>H. A positive control for these studies was BCD-14S, a putative GAG mimic, which at a concentration of 200 μg/ml blocked neurite growth by 94% (data not shown). Free SPA's and underivatized BCD's did not influence neurite growth. Free E SPA reduced viability of neurons to about 21% of control, while survival in the presence of all other free amines was on average 74% of control.

2. SPA-BCD's do not alter neuronal adhesion to poly-D-lysine

The influence of SPA-BCD's on neuronal adhesion to PDL was carried out using naive PC12 cells. Adhesion to PDL was significantly greater (p=0.009) than to plastic alone. However, neither underivatized BCD nor any of the SPA-BCD's had any significant influence on adhesion (Table II).

TABLE II

EFFECTS OF COMPOUNDS ON ADHESION TO POLY-D-LYSINE

| Substrate | Treatment | Adhesion* |
|---|---|---|
| plastic | 0 | 69 + 11& |
| PDL | 0 | 100 + 24 |
| PDL | 5 mM Tris | 90 + 76 |
| PDL | parent BCD | 79 + 13 |
| PDL | G-BCD/Tris | 87 + 16 |
| PDL | G free | 93 + 18 |
| PDL | G-BCD | 104 + 20 |
| PDL | H-BCD | 106 + 13 |

& - significant difference vs PDL

3. SPA-BCD's as substrates

Figure 2:
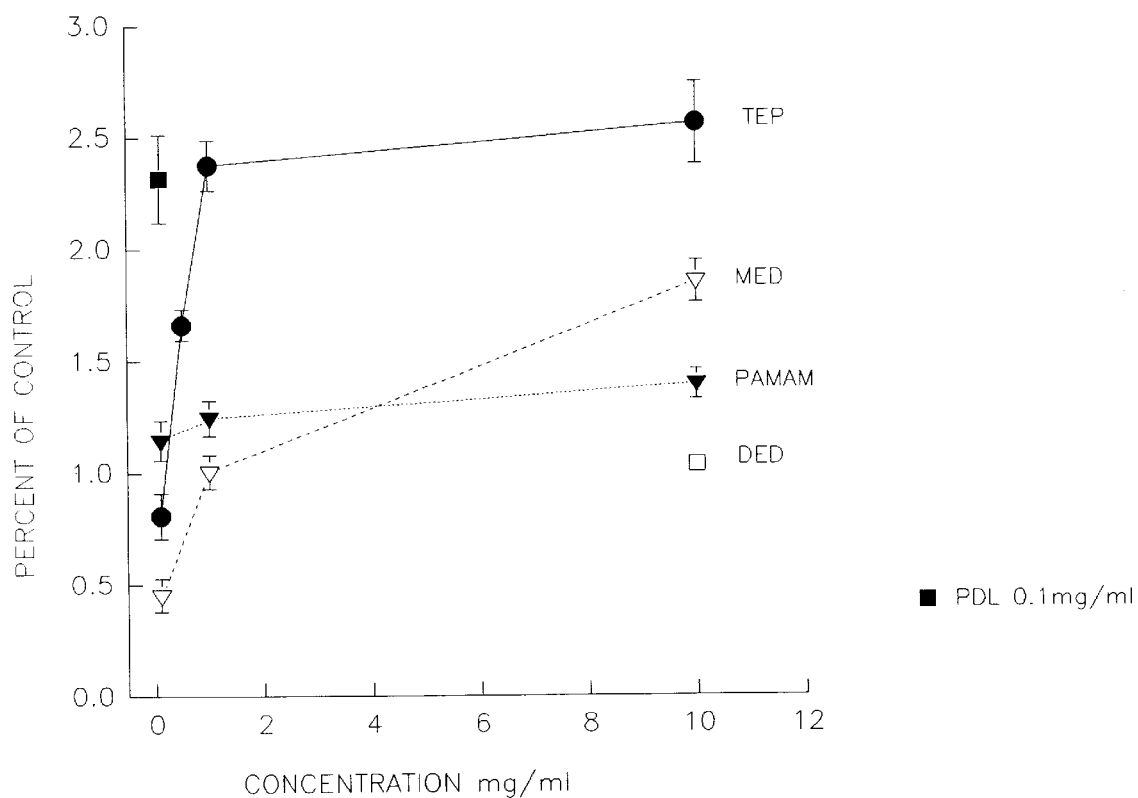
FIG. 2 is a graph illustrating adhesion of PC12 cells to treated plastic. The wells of a 96 well FALCON tissue culture plate were treated overnight with aqueous solutions (at the indicated concentration) of the SPAβCDs. After two washes in sterile distilled water, PC12 cells were seeded in serum-free RPMI and allowed to adhere for 60 minutes at 4 C. After removing medium and washing the wells with phosphate buffered saline, the number of adherent cells was determined by assaying for cellular add phosphatase. The results are expressed as a factor of control -i.e. the number of cells adhering to untreated plastic, and are the results of two experiments (n=6 experiment) and the error bars represent s.e.m.

Adhesion: None of the free amines including PAMAM, or parent BCD had effects on adhesion of PC-12 cells or DRG neurons that differed significantly from the tissue culture plastic substrate. The dose response profile for adhesion of PC-12 cells and DRG neurons by G-BCD was significantly greater than that to plastic, and was saturated at a coating concentration of 0.1 mg/ml. (FIG. 2). For E-BCD significant adhesion for both PC-12 cells and DRG neurons occurred only at a coating concentration of 10 mg/ml. There were no obvious effects of H- and K-BCD's on adhesion of either PC-12 cells or DRG neurons at coating concentrations of 10 mg/ml.

Figure 3:
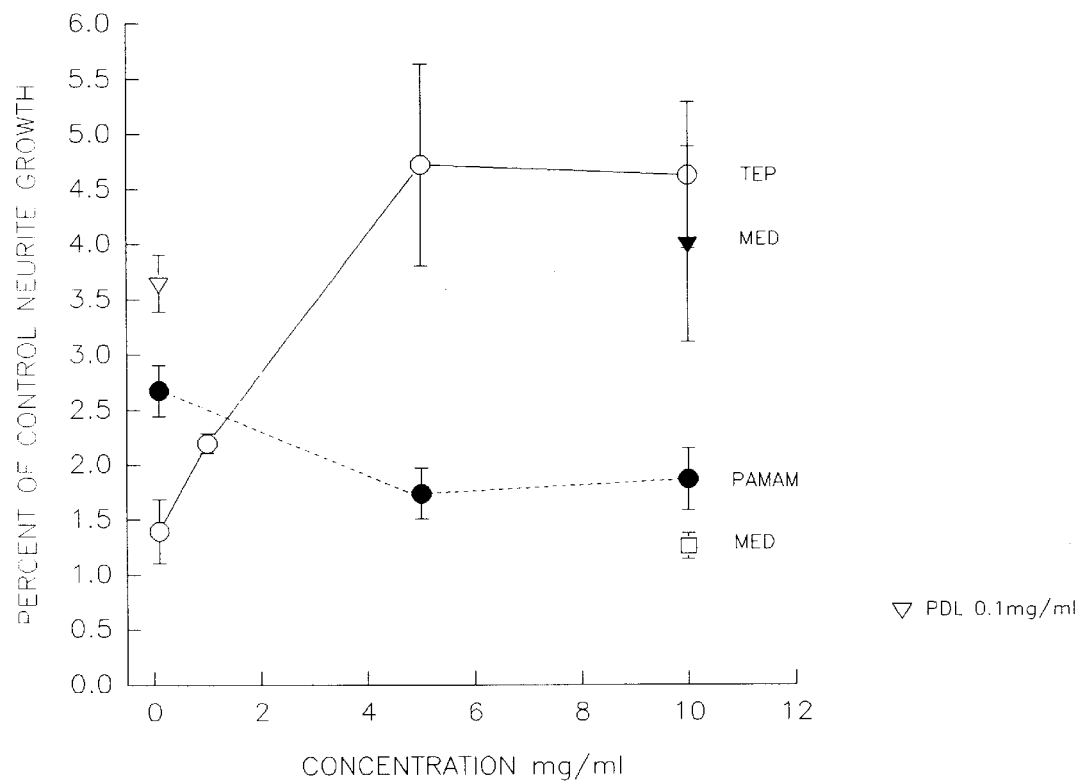
FIG. 3 is a graph illustrating support of neurite growth by ED8 DRG neurons on immobilized SPAβCDS. The wells of a Terasaki plate were coated overnight with the SPAβCDs at the indicated concentration. After washing the wells twice with sterile distilled water and once with culture medium, ED8 chick DRG sensory neurons were seeded into the wells (1000 cells per well) in the presence of 1 ng/ml NGF. Wells were scored blind for % neurite bearing cells and results expressed as a factor of neurite growth on untreated plastic. The results are the mean of three experiments (n=4 per experiment) and error bars represent s.e.m.

Neurite Growth: None of the free amines used to derivatize BCD or the parent BCD had any influence on NGF-mediated neurite growth on a tissue culture plastic substrate. The dose response profile for coating of plastic to support neurite growth by G-BCD demonstrated saturation at 5 mg/ml coating concentration (FIG. 3). At a coating concentration of 10 mg/ml, E-BCD supported the same level of neurite growth as PDL used at 0.1 mg/ml. At 10 mg/ml K-BCD supported approximately 50% of the neurite growth as observed on PDL, and neurite growth supported by H-BCD when used at 10 mg/ml to treat the culture surface was no different than that observed on plastic alone. The starburst amine PAMAM used at 10 mg/ml to coat the substrate was as effective as K-BCD at the same concentration.

Neuronal morphology: Generally, on tissue culture plastic and on the less favourable substrates for adhesion, cell adhesion to surfaces was uneven, and was characterized by a tendency for the cells to clump. Neurites appeared to fasciculate and bridged between the cell aggregates. More even cell dispersal was a feature of PDL and substrates that supported adhesion and neurite growth, and neurites appeared not to fasciculate.

5. Selectivity of substrates of adhesion and growth for glycosaminoglycans: To determine the GAG selectivity of the substrates, G-BCD was chosen as the compound that gave the highest signal-to-noise ratio in adhesion and neurite growth assays, and its properties were compared to those of PDL. Heparin and CS-GAG's were used at concentrations of 10 μg/ml which have been shown previously to distinguish between the effects of HSPG's and CSPG's on a HSPG-selective substrate. As depicted in Table III, on a PDL substrate, cell surface CSPG's were involved in adhesion but not neurite growth, while HS-GAG's were involved in both adhesion and neurite growth. These observations, combined with analyses on binding of PG's to PDL indicate that PDL does not provide a GAG-selective substrate. On the G-BCD substrate however, cell surface CSPG was not involved in either adhesion or neurite growth, whereas cell surface HSPG's contributed to both of these functions. Thus for neurons, the G-BCD compound was HSPG-selective (Table III).

TABLE III

SELECTIVITY OF SUBSTRATES FOR GLYCOSAMINOGLYCANS

% OF CONTROL

| ADDITIVE | NEURITE GROWTH ON | | ADHESION ON | |
|---|---|---|---|---|
| | PDL | G-BCD | PDL | G-BCD |
| CS-GAG's | 109 + 20 | 89 + 22 | 76 + 3 | 99 + 7 |
| Heparin | 68 + 13 | 47 + 4 | 51 + 6 | 43 + 7 |

The principal observation of these studies is that small molecule compounds comprised of soluble polyammonium species coupled covalently to BCD's act as inhibitors of neurite growth on PDL, in part by interfering with the interaction of cell surface HSPG's with this substrate.

On a PDL substrate neuronal cell surface CSPG's and HSPG's were involved in adhesion, but only HSPG was involved in neurite growth. The observation that the SPA-BCD's interfered with neurite growth on PDL with no influence on adhesion suggest that they are HS selective. Such proof was forthcoming for G-BCD which was shown to be a HS selective substrate for neurite growth (and for adhesion).

The finding that HSPG's are involved in neurite growth both on PDL and on G-BCD is consistent with observations that HSPG's are preferentially off-loaded distally from the anterograde axonal transport pool relative to CSPG's, and that HSPG's are less avidly bound to PDL than CSPG's. In other words, HSPG's appear to be in a spatially preferable position within the growth cone to mediate neurite growth, and have (relative to CSPG's) low affinity interactions with PDL that would be required for the dissociation of neurite contact with the substrate of growth necessary for process elongation.

The nature of the GAG-mediated interactions with binding domains in the extra-neuronal milieu that mediate neurite growth have begun to be elucidated in the present studies. A review of published literature on binding motifs within adhesion molecules for GAG's indicates that basic charge is more dense and more uniform in sub-domains of motifs that display CS selectivity. For HS-selective motifs, basic charge density in sub-domains is less because charged residues are separated by longer stretches of more hydrophobic residues (Table IV). To the extent that we have generated compounds that are HS selective, the SPA-BCD's closely mimic HS binding motifs on CAM's.

The synthesis of HS selective small molecule compounds that block neurite growth have implications for CNS disorders where aberrant neurite growth is a disease phenotype, and where HSPG's are implicated. For example, in Alzheimer's disease, synapse loss, aberrant (dystrophic) neurite growth, and neurofibrillary tangle formation are strong correlates of disease severity. HSPG's are molecular constituents of dystrophic neurites and of NFT's. To the extent that dystrophic neurite formation is a disease severity correlate in AD, small molecule HS-selective antagonists of neurite growth may have therapeutic potential.

As will be appreciated for in-vivo administration to a patient in need thereof, the CDs of the present invention may be administered by intravenous injection, intracerebroventricular injection, in a pharmaceutically and physiologically acceptable carrier therefor, such as water, isotonic saline, or encapsulated in a liposome or the like. It will also be appreciated that nerve growth inhibition is important in the treatment and management of epilespy, amyloid diseases such as Alzheimers, and chronic pain syndrome. Nerve growth stimulation is important in the treatment of spinal cord injuries, peripheral nerve injuries, diabetes, chemotherapy exposure and stroke among others.

We claim:

1. A process for producing homogeneous cyclodextrin derivatives of the formula

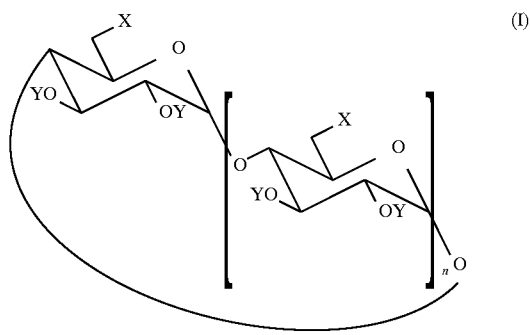

in which n is an integer from 5 to 12;

X is selected from the group consisting of $NH_2$, $NH_3Q$, $NH_2RQ$, $NHR_2Q$, $NR_3Q$, $NHRR^1Q$, $NRR^1R^2Q$, $NR_2R^1Q$, $CH_2NH_2$, $CH_2NH_3Q$, $CH_2NH_2RQ$, $CH_2NHR_2Q$, $CH_2NR_3Q$, $CH_2NHRR^1Q$, $CH_2NRR^1R^2Q$, $CH_2NR_2R^1Q$, $SR^3$ and $SO_3^-Z^+$;

Y is selected from H, alkyl or carboxyl ester chains containing from 1–20 carbon atoms which may contain nitrogen and unsaturations;

where R, $R^1$ and $R^2$ are the same or different containing 1–20 carbon atoms, 1–10 nitrogen atoms, 1–4 oxygen atoms, and 4–80 hydrogen atoms, 1–10 counterions, and moieties in which C,H and N are present in a heterocyclic ring;

or $C_3H_6SO_3Z$;

$R^3$ is H or R;

Q is an anionic counterion; and

Z is a cation selected from the group consisting of proton, sodium potassium or trialkylammonium; comprising reacting a cyclodextrin as defined above but bearing free hydroxyl groups at the carbon-6 position with a compound of the formula:

where R" is an alkyl containing 1–5 carbon atoms; and X' is a halogen selected from the group consisting of bromine and iodine, so as to produce a halogenated derivative, and converting said halogenated derivative to a selected said homogeneous cyclodextrin derivative by substitution or exchange of said X' at carbon 6.

2. A process as claimed in claim 1 in which said halogenated derivative is reacted with an alkali metal sulfite salt under pressure so as to produce a homogeneous cyclodextrin derivative having a sulfonyl group at each primary face carbon-6 position.

3. A process as claimed in claim 1 in which said halogenated derivative is reacted with an alkali metal azide salt and reduced to yield a homogeneous derivative having an amino group at each primary face carbon-6 position.

4. A process as claimed in claim 1 in which said halogenated derivative is reacted with an alkali metal cyanide salt and reduced to yield homogeneous amino derivative having an aminomethylene group at each primary face carbon-6 position.

5. A process as claimed in claim 1 wherein said halogenated derivative is reacted with thiourea so as to produce a thiouronium derivative having a thiouronium group at each primary face carbon-6 position, and said thiouronium derivative is hydrolysed or alcoholized so as to produce a homogeneous mercapto derivative having a mercapto or thiol group at each primary face carbon-6 position.

6. A process as claimed in claim 5 wherein said mercapto derivative is reacted with an alkyl halide so as to produce a homogeneous mercaptoamine derivative having a sulfide functionality at each primary face carbon-6 position.

7. A process as claimed in claim 1 wherein said halogenated derivative is reacted with an amine so as to produce a homogeneous derivative having an amine functionality at each primary face carbon-6 position.

8. A process as claimed in claim 3 wherein said amino derivative is reacted with an aldehyde so as to produce a homogenous mercapto derivative having a mercapto or thiol group at each primary face carbon-6 position.

9. A method for modulating nerve process growth comprising administering to a patient in need thereof a homogeneous cyclodextrin derivative of the formula

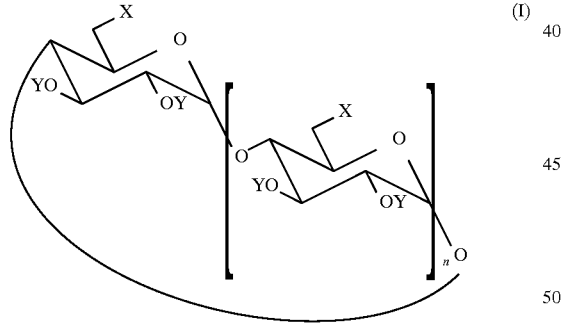

(I)

in which n is an integer from 5 to 12;

X is selected from the group consisting of $NH_2$, $NH_3Q$, $NH_2RQ$, $NHR_2Q$, $NR_3Q$, $NHRR^1Q$, $NRR^1R^2Q$, $NN_2R^1Q$, $CH_2NH_2$, $CH_2NH_3Q$, $CH_2NH_2RQ$, $CH_2NHR_2Q$, $CH_2NR_3Q$, $CH_2NHRR^1Q$, $CH_2NRR^1R^2Q$, $CH_2NR_2R^1Q$, $SR^3$ and $SO_3^-Z^-$;

Y is selected from H, alkyl or carboxyl ester chains containing from 1–20 carbon atoms which may contain nitrogen and unsaturations;

where R, $R^1$ and $R^2$ are the same or different containing 1–20 carbon atoms, 1–10 nitrogen atoms, 1–4 oxygen atoms, and 4–80 hydrogen atoms, 1–10 counterions, and moieties in which C, H and N are present in a heterocyclic ring; or $C_3H_6SO_3Z$;

$R^3$ is H or R;

Q is an anionic counterion; and

Z is a cation selected from the group consisting of proton, sodium potassium or trialkylammonlum in admixture with a pharmaceutically acceptable carrier thereof.

10. A therapeutic compound according to claim 9, wherein said modulating step comprises inhibition of nerve process growth.

11. A therapeutic compound according to claim 9, wherein said nerve process growth comprises neurite growth.

12. A homogeneous cyclodextrin derivative of the formula

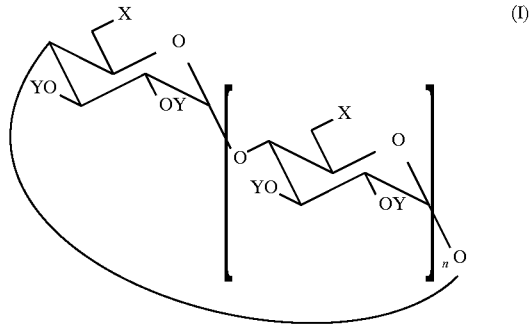

(I)

in which n is an integer from 5 to 12;

X is selected from the group consisting of $NH_2RQ$, $NHR_2Q$, $NR_3Q$, $NHRR^1Q$, $NRR^1R^2Q$, $NR_2R^1Q$, $CH_2NH_2$, $CH_2NH_3$, $CH_2NH_2RQ$, $CH_2NHR_2Q$, $CH_2NR_3Q$, $CH_2NHRR^1Q$, $CH_2NRR^1R^2Q$, $CH_2NR_2R^1Q$, and $SR^3$;

Y is selected from H, alkyl or carboxyl ester chains containing from 1–20 carbon atoms which may contain nitrogen and unsaturations;

where R, $R^1$ and $R^2$ are the same or different containing 1–20 carbon atoms, 1–10 nitrogen atoms, 1–4 oxygen atoms, and 4–80 hydrogen atoms, 1–10 counterions, and moieties in which C, H and N are present in a heterocyclic ring; or $C_3H_5SO_3Z$;

$R^3$ is H or R, with the proviso that said R is not $C_6H_5$ or a simple alkyl substituted benzene ring where said R is $C_6H_4$-alkyl or $C_6H_3$-(alkyl)$_2$;

with the proviso that, when X=$NH_2RQ$ or $NHR_2Q$, R is not an unbranched alkyl chain, nor an unbranched alkyl chain bearing one hydroxyl group;

and with the proviso that X is not selected from a piperidine, N-methyl piperazine, adenine, imidazole, histamine, mercaptomethyl imidazole, pyridoxamine, thiourea; and with the proviso that when X=SR, R is not a C1–C10 benzene derivative nor aminoethyl;

Q is an anionic counterion; and

Z is a cation selected from the group consisting of proton, sodium potassium or trialkylammonium.

13. A homogeneous amino cyclodextrin derivative as claimed in claim 11 derivatized with an amino where X is selected from the group consisting of $NHCH_2CH_2NH_2$ $HNCH_2CH_2NHCH_2CH_2NH_2$ $HNCH(CH_2OH)_2$ $(R^4)_2NCH_2CH_2NH$, ($R^4$=Me, Et)

$NH_2CH_2C\ H_4N$, or salts thereof.

14. A method as claimed in claim 13 wherein said homogeneous cyclodextrin derivative is an amino cyclodextrin derivatized with an amine selected from the group consisting of
$NHCH_2CH_2NH_2$
$HNCH_2CH_2NHCH_2CH_2NH_2$
$HNCH(CH_2OH)_2$
$(R^4)_2NCH_2CH_2NH_2$, ($R^4$=Me, Et)
$NH_2CH_2C_5H_4N$
or salts thereof.

* * * * *

UNITED STATES PATENT AND TRADEMARK OFFICE
CERTIFICATE OF CORRECTION

PATENT NO.: 5,834,446

DATED: November 10, 1998

INVENTORS: Kimberly E. DOW, Boris I. GORINE, Richard J. RIOPELLE and Gregory THATCHER It is certified that error appears in the above-identified patent and that said Letters Patent is hereby corrected as shown below:

In claim 1, column 14, line 58, "$R''_2NCHX'+X'^-$" should be --$R''_2NCHX'^+X'^-$--.

In claim 9, column 15, line 56, "$NN_2R'Q$," should be --$NR_2R'Q$,--.

In claim 9, column 15, line 58, "$SO_3^-Z^-$;" should be --$SO_3^-Z^+$;--.

In claim 12, column 16, line 31, "$CH_2NH_3$," should be --$CH_2NH_3Q$,--.

In claim 12, column 16, line 41, "$C_3H_5SO_3Z$;" should be --$C_3H_6SO_3Z$;--.

In claim 13, column 16, line 59, "11" should be --12--.

In claim 13, column 16, line 66, "$NH_2CH_2C\ H_4N$," should be --$NH_2CH_2C_5H_4N$,--.

In claim 14, column 17, line 1, "13" should be --9--.

Signed and Sealed this

Sixteenth Day of March, 1999

Attest:

Q. TODD DICKINSON

*Attesting Officer*  *Acting Commissioner of Patents and Trademarks*